United States Patent
Fred et al.

(10) Patent No.: US 11,544,907 B2
(45) Date of Patent: Jan. 3, 2023

(54) SYSTEMS AND METHODS FOR AUGMENTED-OR VIRTUAL REALITY-BASED DECISION-MAKING SIMULATION

(71) Applicants: Tanner Fred, Shirley, NY (US); Joseph Fields, Shirley, NY (US)

(72) Inventors: Tanner Fred, Shirley, NY (US); Joseph Fields, Shirley, NY (US)

(*) Notice: Subject to any disclaimer, the term of this patent is extended or adjusted under 35 U.S.C. 154(b) by 0 days.

(21) Appl. No.: 17/242,574

(22) Filed: Apr. 28, 2021

(65) Prior Publication Data
US 2021/0343084 A1 Nov. 4, 2021

Related U.S. Application Data

(60) Provisional application No. 63/017,859, filed on Apr. 30, 2020.

(51) Int. Cl.
*G06T 19/00* (2011.01)

(52) U.S. Cl.
CPC .......... *G06T 19/003* (2013.01); *G06T 19/006* (2013.01)

(58) Field of Classification Search
CPC ............................ G06T 19/003; G06T 19/006
See application file for complete search history.

(56) References Cited

U.S. PATENT DOCUMENTS

| | | | |
|---|---|---|---|
| 10,475,351 B2 * | 11/2019 | Horseman | A61B 5/165 |
| 11,176,465 B2 * | 11/2021 | Hazard | G06K 9/6277 |
| 11,295,131 B1 * | 4/2022 | Dhawan | G05B 13/027 |
| 11,361,664 B2 * | 6/2022 | Grabowski | G06T 11/00 |

(Continued)

FOREIGN PATENT DOCUMENTS

| | | |
|---|---|---|
| CN | 107261504 A | 10/2017 |
| KR | 101736440 B1 | 5/2017 |
| KR | 20180077588 A | 7/2018 |

OTHER PUBLICATIONS

Sharma et al., Megacity: A collaborative Virtual Reality Environment for Emergency Response, Training, and Decision Making, Society for Imaging Science and Technology, pp. 70-77, 2017 (Year: 2017).* International Search Report and Written Opinion issued by the ISA/US in connection with International Application No. PCT/US2021/029542 dated Jul. 22, 2021.

*Primary Examiner* — Motilewa Good-Johnson
(74) *Attorney, Agent, or Firm* — Carter, DeLuca & Farrell LLP; George Likourezos

(57) ABSTRACT

A system for display for an augmented/virtual reality-based decision-making simulation includes a controller configured to receive input from a user, at least one of an augmented reality or a virtual reality device configured to display a simulated environment, a processor, and a memory coupled to the processor. The memory stores one or more computer-readable instructions, which, when executed by the processor, cause the system to: receive input by the user from the controller, indicating a selected scenario; display, on the at least one of the augmented reality or the virtual reality device, the selected scenario; receive input from the user, from the controller, to interact with the selected scenario; monitor one or more parameters associated with the execution of tasks in the selected scenario using the controller; and evaluate the user based on the monitored one or more parameters.

18 Claims, 3 Drawing Sheets

(56) References Cited

U.S. PATENT DOCUMENTS

| | | | |
|---|---|---|---|
| 2002/0010734 A1* | 1/2002 | Ebersole | H04L 67/36 |
| | | | 709/201 |
| 2013/0203026 A1 | 8/2013 | Sundaresh et al. | |
| 2013/0314303 A1* | 11/2013 | Osterhout | G06F 3/017 |
| | | | 345/8 |
| 2014/0130076 A1 | 5/2014 | Moore et al. | |
| 2016/0077547 A1 | 3/2016 | Aimone et al. | |
| 2016/0378861 A1 | 12/2016 | Eledath et al. | |
| 2017/0221267 A1* | 8/2017 | Tommy | G09B 5/125 |
| 2017/0293356 A1* | 10/2017 | Khaderi | A61B 3/024 |
| 2018/0075293 A1* | 3/2018 | Sehinas | G06T 19/006 |
| 2018/0173309 A1 | 6/2018 | Uchiyama et al. | |
| 2018/0247560 A1* | 8/2018 | Mackenzie | A61B 16/00 |
| 2018/0293802 A1* | 10/2018 | Hendricks | G09B 23/30 |
| 2019/0146577 A1* | 5/2019 | Rokade | G09B 5/02 |
| | | | 345/156 |
| 2019/0189023 A1* | 6/2019 | Salinas Vela | G09B 9/00 |
| 2019/0206134 A1* | 7/2019 | Devam | G06T 19/00 |
| 2019/0244427 A1* | 8/2019 | Sun | G06F 3/011 |
| 2019/0255419 A1 | 8/2019 | Reilly et al. | |
| 2019/0259292 A1* | 8/2019 | Williams | G09B 5/06 |
| 2019/0354765 A1 | 11/2019 | Chan et al. | |
| 2019/0392728 A1* | 12/2019 | Pike | G06T 19/003 |
| 2020/0013311 A1* | 1/2020 | Rosenberg | G09B 19/00 |
| 2020/0089321 A1* | 3/2020 | Kacelenga | G06F 3/011 |
| 2020/0193854 A1* | 6/2020 | Salinas Vela | G09B 5/125 |
| 2020/0372821 A1* | 11/2020 | Mercer | G06F 3/0488 |
| 2020/0388177 A1* | 12/2020 | Recker | G06F 3/011 |
| 2020/0410286 A1* | 12/2020 | Fox | G06N 3/084 |
| 2021/0110293 A1* | 4/2021 | Lehr | G06K 9/6282 |
| 2021/0216770 A1* | 7/2021 | Kang | H04W 4/38 |
| 2021/0294944 A1* | 9/2021 | Nassar | B60W 50/00 |

* cited by examiner

SYSTEMS AND METHODS FOR AUGMENTED-OR VIRTUAL REALITY-BASED DECISION-MAKING SIMULATION

CROSS-REFERENCE TO RELATED APPLICATIONS

This application claims the benefit of U.S. Provisional Patent Application No. 63/017,859, filed on Apr. 30, 2020, the entire contents of each of which are hereby incorporated herein by reference.

TECHNICAL FIELD

The present application relates to systems and methods for an augmented reality or virtual reality simulation and, in particular, to an augmented reality or virtual reality decision-making simulation.

BACKGROUND

Obtaining practical experience in stressful situations in the past generally has involved basic models that often do not have any dynamic form of interaction. For example, training situations may use humans acting as injured individuals in mass trauma simulations with cards telling them what their respective injuries are and what to do. A problem with these simulations is that the injuries are static (such as a wound being simulated by liquid-soaked clothes possibly with make-up) with the actor providing additional feedback and information in response to the treatment received.

Therefore, a need exists for augmented reality or virtual reality decision-making simulations.

SUMMARY

This disclosure relates to systems and methods for an augmented/virtual reality-based decision-making simulation. In accordance with aspects of the present disclosure, a system for display for an augmented/virtual reality-based decision-making simulation includes a controller configured to receive input from a user, at least one of an augmented reality or a virtual reality device configured to display a simulated environment, a processor, and a memory coupled to the processor. The memory stores one or more computer-readable instructions, which, when executed by the processor, cause the system to: receive user input from the controller, indicating a selected scenario; display, on the at least one of the augmented reality or the virtual reality device, the selected scenario; receive input from the controller, indicating user interaction with the selected scenario; monitor one or more parameters associated with the execution of tasks in the selected scenario using the controller; and evaluate the user based on the monitored one or more parameters.

In an aspect of the present disclosure, the evaluation may be performed using machine learning.

In an aspect of the present disclosure, the instructions, when executed by the processor, may further cause the system to display, on at least one of the augmented reality or the virtual reality display, a layout of decisions that were made by the user during the selected scenario.

In another aspect of the present disclosure, the instructions, when executed by the processor, may further cause the system to display, on at least one of the augmented reality or the virtual reality display, a walk-through of the layout.

In yet another aspect of the present disclosure, the instructions, when executed by the processor, may further cause the system to display, on at least one of the augmented reality or the virtual reality display, an indication of how one or more major decisions impacted an outcome of the selected scenario.

In a further aspect of the present disclosure, the selected scenario may include: being in a top floor of a building that is on fire; being inside a school where there is an active shooter; waking up to find somebody has broken into a home of the user and is still there; a phobia of spiders; a phobia of heights; being lost in a forest; and/or being a passenger on a plane.

In yet a further aspect of the present disclosure, the system may further include a heart rate monitor configured to generate a signal indicative of a heart rate of the user.

In an aspect of the present disclosure, the instructions, when executed by the processor, may further cause the system to receive the signal from the heart rate monitor and modify the simulated environment based on the signal.

In another aspect of the present disclosure, the at least one of the augmented reality or the virtual reality device may further include a sensor configured to sense head movement and communicate to the processor a signal indicative of a head movement of the user. The instructions, when executed by the processor, may further cause the system to receive further input from the at least one of the augmented reality or the virtual reality device based on the user's head movements and move the user in the simulated environment based on the further input.

In yet another aspect of the present disclosure, the instructions, when executed by the processor, may further cause the system to display on the at least one of the augmented reality or the virtual reality device, an indication of the input chosen by the user.

In accordance with aspects of the present disclosure, a computer-implemented method for an augmented/virtual reality-based decision-making simulated environment, includes: receiving, from a controller configured to receive input from a user, user input indicating a selected scenario; displaying, on at least one of an augmented reality or a virtual reality device, the selected scenario; receiving input from the controller, indicating user interaction with the selected scenario; monitoring one or more parameters associated with the execution of tasks in the selected scenario using the controller; and evaluating the user based on the monitored one or more parameters.

In an aspect of the present disclosure, the evaluation may be performed using machine learning.

In another aspect of the present disclosure, the method may further include displaying, on at least one of the augmented reality or the virtual reality display, a layout of decisions that were made by the user during the selected scenario.

In yet another aspect of the present disclosure, the method may further include displaying, on at least one of the augmented reality or the virtual reality display, a walk-through of the layout.

In a further aspect of the present disclosure, the method may further include displaying, on at least one of the augmented reality or the virtual reality display, an indication of how one or more major decisions impacted an outcome of the selected scenario.

In yet a further aspect of the present disclosure, receiving input by a user indicating a selected scenario may include indicating a scenario selected from: being in a top floor of a building that is on fire; being inside a school where there is an active shooter; waking up to find somebody has broken into a home of the user, and is still there; a phobia of spiders; a phobia of heights; being lost in a forest; or being a passenger on a plane.

In an aspect of the present disclosure, the method may further include receiving a signal from a heart rate monitor configured to generate a signal indicative of a heart rate of the user and modifying the simulated environment based on the signal.

In another aspect of the present disclosure, the at least one of the augmented reality or the virtual reality device further may include a sensor configured to sense head movement. The computer-implemented method may further include receiving further input from the at least one of the augmented reality or the virtual reality device based on the user's head movements and moving the user in the simulated environment based on the further input.

In yet another aspect of the present disclosure, the method may further include displaying on the at least one of the augmented reality or the virtual reality device an indication of the input chosen by the user.

In accordance with aspects of the present disclosure, a non-transitory computer-readable storage medium in which is stored instructions for causing a processor to execute a computer-implemented method for an augmented/virtual reality-based decision-making simulated environment is presented. The method includes: receiving, from a controller configured to receive input from a user, user input indicating a selected scenario; displaying, on at least one of an augmented reality or a virtual reality display, the selected scenario; receiving input from the controller, indicating user interaction with the selected scenario; monitoring one or more parameters associated with the execution of tasks in the selected scenario using the controller; and evaluating the user based on the monitored one or more parameters.

Further details and aspects of exemplary embodiments of the present disclosure are described in more detail below with reference to the appended figures.

BRIEF DESCRIPTION OF THE DRAWINGS

A better understanding of the features and advantages of the disclosed technology will be obtained by reference to the following detailed description that sets forth illustrative embodiments, in which the principles of the technology are utilized, and the accompanying drawings of which.

DETAILED DESCRIPTION

Figure 1:
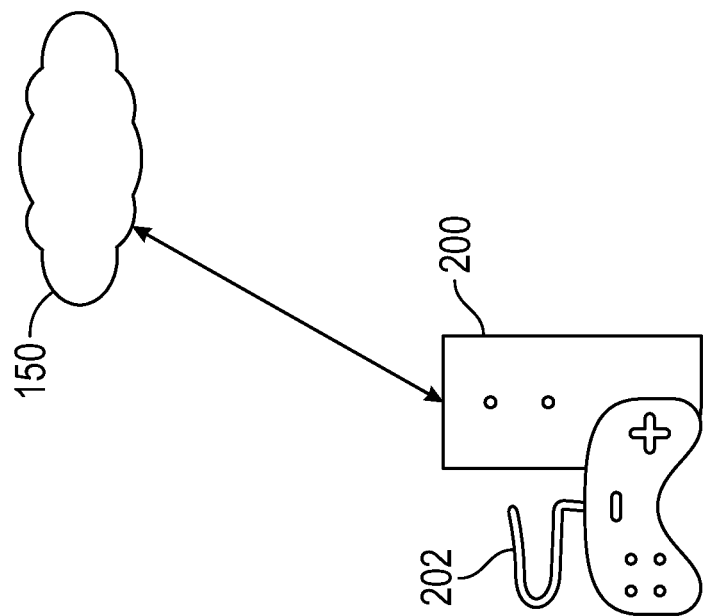
FIG. 1 is a network diagram illustration showing an exemplary game system for a computer-implemented method for an augmented reality or virtual reality decision-making simulated environment in accordance with aspects of the present disclosure.
Figure 1:
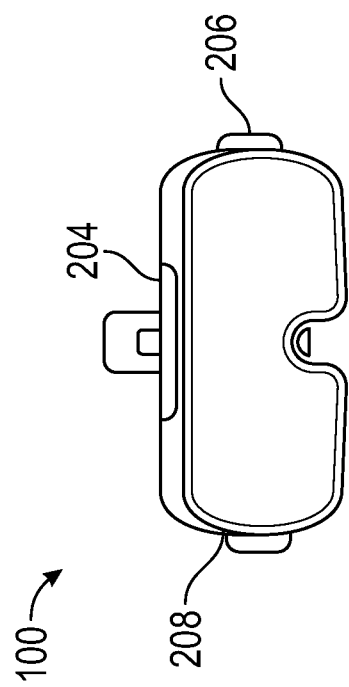

The present application relates to systems and methods for an augmented reality or virtual reality simulation, and in particular, to an augmented reality or virtual reality decision making simulation.

For purposes of promoting an understanding of the principles of the present disclosure, reference will now be made to exemplary embodiments illustrated in the drawings, and specific language will be used to describe the same. It will nevertheless be understood that no limitation of the scope of the present disclosure is thereby intended. Various alterations, rearrangements, substitutions, and modifications of the inventive features illustrated herein, and any additional applications of the principles of the present disclosure as illustrated herein, which would occur to one skilled in the relevant art and having possession of this disclosure, are to be considered within the scope of the present disclosure.

Referring to FIG. 1, an exemplary system 100 in accordance with aspects of the present disclosure includes a game system 200, a Virtual Reality (VR) or Augmented Reality (AR) headset device 204, a hand controller 202, and headphones 206 to immerse one or more users in the simulated environment. It is contemplated that the hand controller 202 may be any suitable type for playing AR/VR games and/or simulations. It is contemplated that the game system 200 may run programs remotely via a network 150, over the cloud, or on a remote server. The game system 200 may include, but is not limited to, a gaming console, a personal computer, a tablet, and/or a handheld device. The Virtual Reality (VR) or Augmented Reality (AR) headset device 204 may include a sensor 208 configured to sense the movement of a user's head.

The network 150 may be wired or wireless and can utilize technologies such as Wi-Fi®, Ethernet, Internet Protocol, 3G, 4G, 5G, TDMA, CDMA, or other communication technologies. The network 150 may include, for example, but is not limited to, a cellular network, residential broadband, satellite communications, private network, the Internet, local area network, wide area network, storage area network, campus area network, personal area network, or metropolitan area network.

The term "application" may include a computer program designed to perform particular functions, tasks, or activities for the benefit of a user. Application may refer to, for example, software running locally or remotely, as a stand-alone program or in a web browser, or other software that would be understood by one skilled in the art to be an application. An application may run on the game system 200, a server, or on a user device, including, for example, on a mobile device 140 or a client computer system 110.

Figure 2:
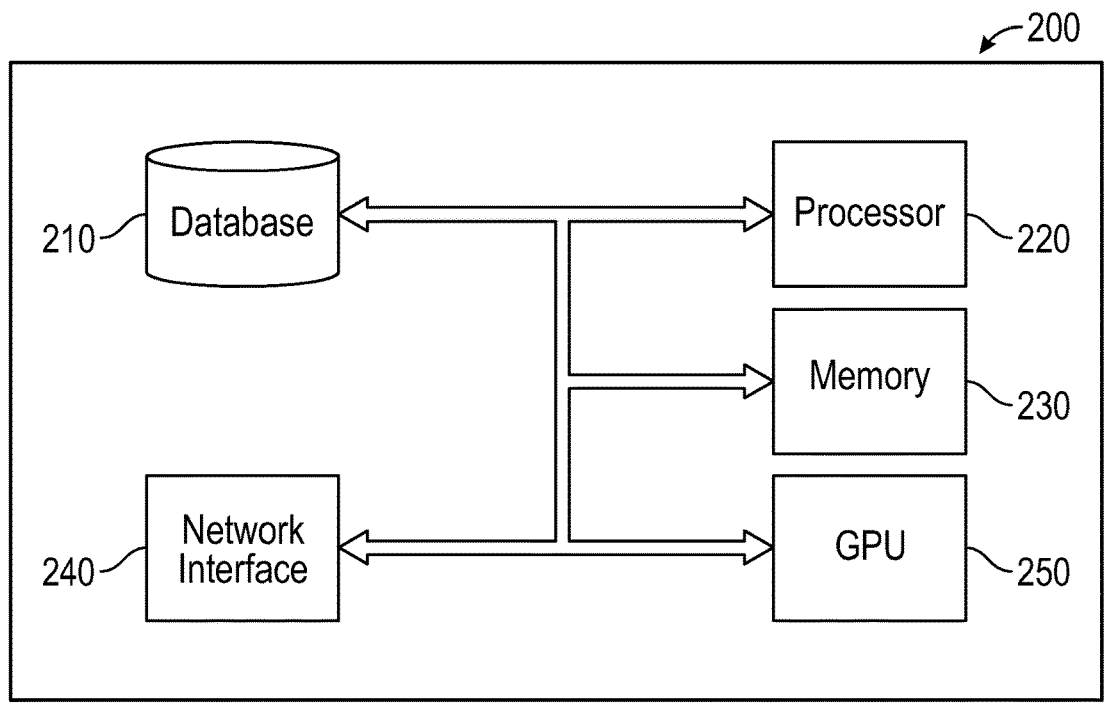
FIG. 2 is a block diagram of an exemplary game system in accordance with aspects of the present disclosure.

Referring now to FIG. 2, exemplary components in the game system 200 in accordance with aspects of the present disclosure include, for example, a database 210, one or more processors 220, at least one memory 230, and a network interface 240.

The database 210 can be located in storage. The term "storage" may refer to any device or material from which information may be capable of being accessed, reproduced, and/or held in an electromagnetic or optical form for access by a computer processor. Storage may be, for example, volatile memory such as RAM, non-volatile memory, which permanently hold digital data until purposely erased, such as flash memory, magnetic devices such as hard disk drives, and optical media such as a CD, DVD, Blu-ray disc, or the like.

In some exemplary systems of the present disclosure, a web interface may run on the game system 200, where the interface includes a calendar application. In various embodiments, data may be stored on the game system 200, including, for example, user tasks, preferences, schedule appointments, historical data, past weather, documents, and/or other data. The data can be stored in the database 210 and sent via the system bus to the processor 220.

As will be described in more detail later herein, the processor 220 executes various processes based on instructions that can be stored in the server memory 230 and utilizing the data from the database 210. With reference also to FIG. 1, a request from a user device, such as a mobile device or a client computer, can be communicated to the server through the server's network interface 240.

Figure 3:
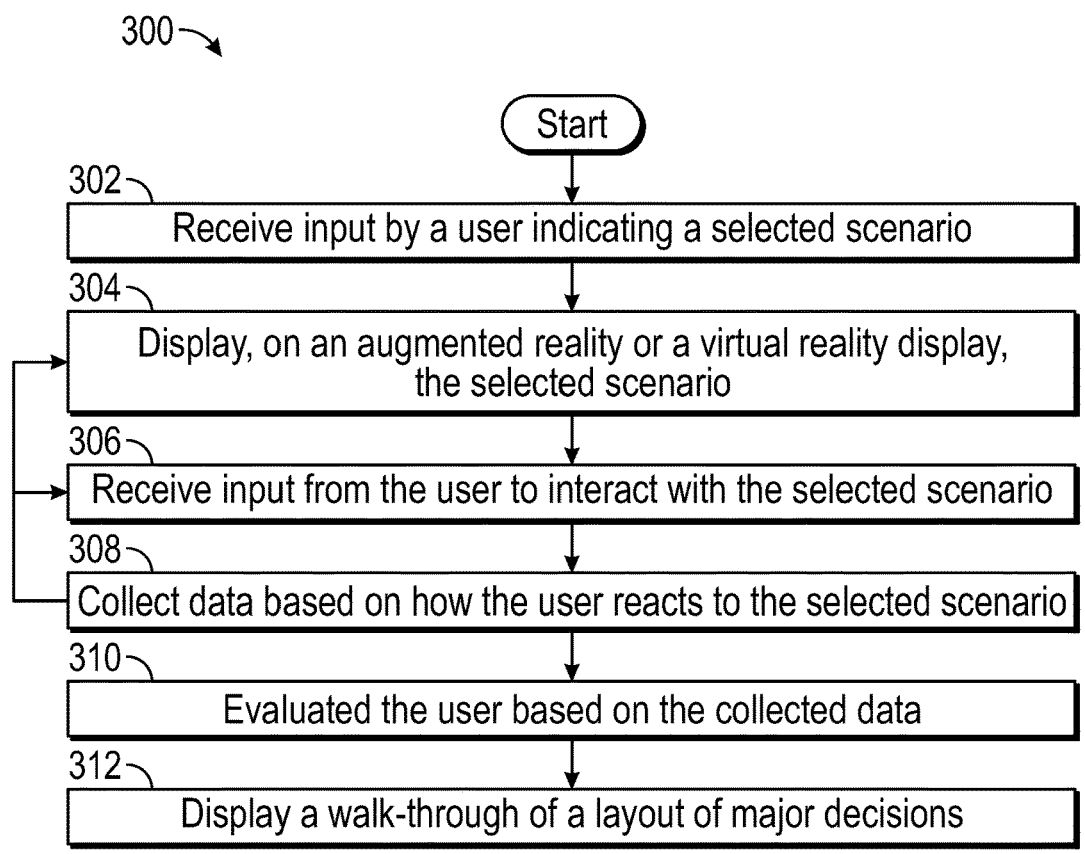
FIG. 3 is an flow diagram of an exemplary method for using the networked environment of FIG. 1.

FIG. 3 shows a block diagram for an exemplary method for an augmented/virtual reality-based decision-making simulation. The method provides a user the opportunity to insert him or herself into a situation that they normally would not want to be in, in their actual lives. The method includes a simulated environment that allows the user to determine how they would react in situations that are either life-threatening or very uncomfortable. Some of these situations include, for example: being on the top floor of a building that is on fire, being inside a school where there is an active shooter, and/or waking up to find somebody has broken into your home and is still there. These situations may be used to not only help the user establish what they "might" do in these circumstances but also to assist in quelling any fears that they might have regarding any of these situations.

In these scenarios, the user has free reign of the entire area and may choose where to go and what they want to do. The situation and outcome changes depending on what decisions the user makes as he or she progresses through each "level." The simulated environment is realistic as possible so that the user can try to be as invested in the virtual reality as the technology allows.

Figure 4:
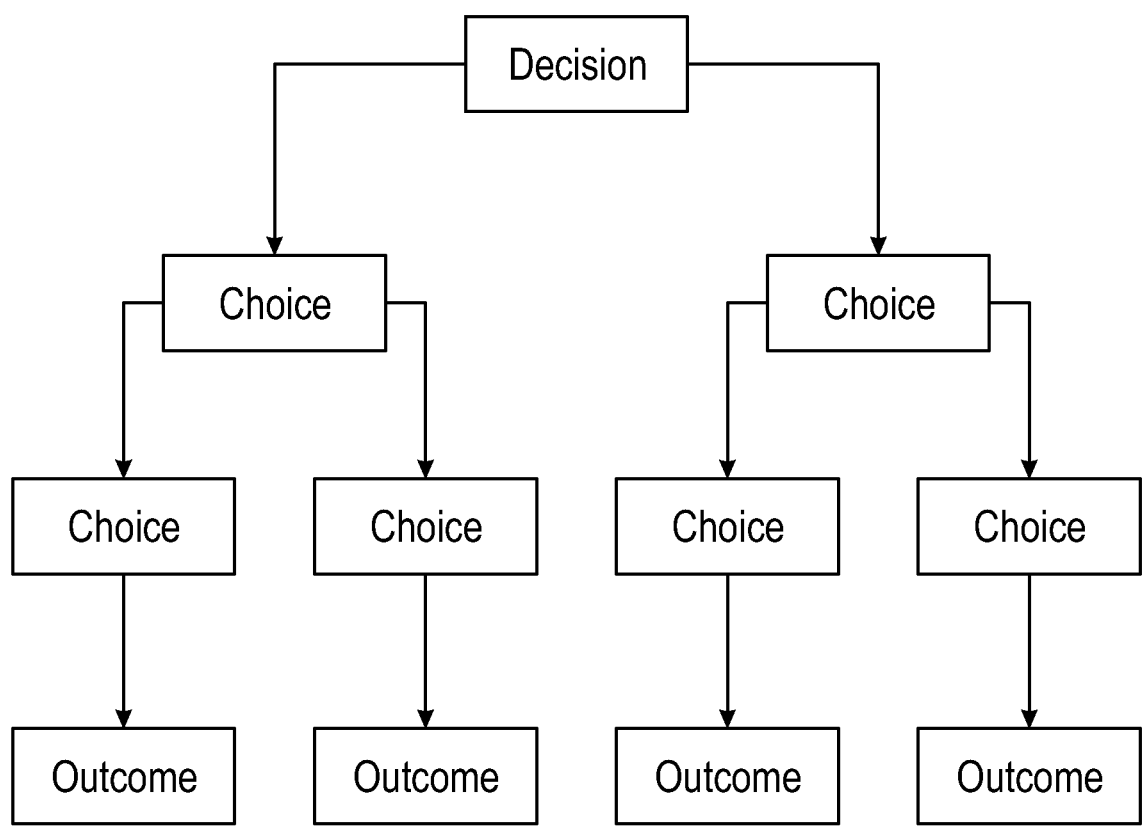
FIG. 4 is an exemplary diagram of an embodiment of the system of FIG. 1.

The simulated environment may include a butterfly-effect style, where the decisions of the user directly affect the direction in which each particular situation heads, and what outcome might be attained. Each choice/decision a user makes may impact the future choices they have able to make. (See FIG. 4)

The simulated environment may be playable on any game system 200 that will support a Virtual Reality (VR) application. The user may use the Augmented Reality (AR) or VR device 204 (FIG. 1), hand controllers, and headphones to immerse themselves in the simulated environment.

The AR/VR device 204 may include sensors configured to sense head movement and communicate to the processor a signal indicative of the user's head movement. For example, the system 100 may detect the user's head movements and determine which direction the character in the simulated environment looks based on the AR/VR device 204. For example, if the user turned his head to the right, the system would detect that movement, and the character in the simulated environment would look to the right. The hand controllers may be used to select scenarios, to move the character around, as well as interact with different objects in the level. The system 100 may include a heart rate monitor configured to monitor the user's heart rate during the simulated environment. The system 100 may receive a signal indicating the heart rate of the user from a user device (e.g., a smart switch). For example, the system 100 may receive an elevated heart rate (e.g., 120 beats per minute) from the heart rate monitor and adjust the simulated environment by either increasing or decreasing the difficulty of the scenario.

The system 100 includes a virtual reality system-based decision-making simulated environment where the user selects the situation which they wish to simulate and to which the user wants to learn how to respond. The user then plays through the situation they have selected. The system 100 may evaluate the user based on the decisions they made.

Initially, at step 302, the processor 220 receives input by a user indicating a selected scenario. The input may include input from a hand controller or the AR/VR device 204. The selected scenario may include, for example, being on a top floor of a building that is on fire, being inside a school where there is an active shooter, waking up to find somebody has broken into the user's home and is still there, a phobia of spiders, a phobia of heights, being lost in a forest, simulating drowning, being in a natural disaster (e.g., an earthquake, a tornado, a hurricane, and/or a tsunami), being a passenger on a plane, and/or phobias of other things. For example, a scenario that includes a phobia of spiders may include, for example, holding a virtual spider, letting it crawl around on the user. For example, a scenario that includes a phobia of heights may include having the user walk on a tightrope across two buildings. For example, a scenario that includes being lost in a forest may include the tasks of finding food, making a fire to keep warm, and/or trying to survive. For example, a scenario that includes being a passenger on a plane that is crashing may include finding oxygen masks and/or trying to survive. In aspects, for scenarios regarding specific phobias, the gameplay for that scenario may include being in a more rigid and pre-written structure. The object of these phobias may include reacting to the movements and reactions of the user, but it may not be in a controlled environment and would not be in an open-ended manner.

Next, at step 304, the processor 220 displays, on an AR/VR device 204, the selected scenario. For example, the displayed scenario may include an open world simulated environment of a school and the surrounding environment.

Next, at step 306, the processor 220 receives input from the user to interact with the selected scenario. For example, if the selected scenario is waking up to find somebody has broken into your home and is still there, then the user may have to choose things like calling the police, arming themselves, or locking themselves in a room.

The processor at step 308 collects data based on how the user reacts to the selected scenario. For example, as the user makes any significant decisions, the processor collects the data on these decisions and timing related to the decisions.

Next, at step 310, the processor 220 evaluates the user based on the collected data. In aspects, the processor 220 may provide haptic feedback, via the controller and/or the AR/VR device 204, based on the evaluation.

At step 312, the processor 220 displays, on a display, a layout of any significant decisions that were made by the user during the selected scenario; a walk-through of the layout; and an indication of why other choices for some of the significant decisions may have been better and could have increased the user's survivability. The system 100 may use a percentage-based system 100 that may inform the user of their chance of survival. In aspects, the user may not be informed of which decisions would have resulted in a higher percentage score, so that the user may return to the game and attempt alternative decisions. For example, the user may receive a percentage score for each decision made through the scenario so the user could visually see how their score fluctuated throughout the scenario and develop conclusions on their own about how they could change their outcome.

The evaluations of the user may not inform the user how to be better initially but instead provide a layout of the major decisions that were made and the resulting outcome. After a level is completed, the user is walked through their decisions and shown why some other decisions may have increased their survivability. Evaluations may be determined based on other user's experiences as recorded by the processor. For example, as other users get further and further in the simulated environment, the processor records and then uses this data when evaluating the user's decisions. The processor may include a machine-learning algorithm configured to make these evaluations. The machine-learning algorithm may be trained using existing user data and/or other user data. In aspects, the machine-learning algorithm used would run through the scenario multiple times on its own, and the results may be gathered in addition to feedback and advice from potential experts in the field and then combined to determine which routes on a scenario would wield the greatest results. The machine learning algorithm may include a convolutional neural network and/or a state variant machine (SVM). The machine learning algorithm may be trained using supervised training and/or unsupervised training.

These situations are presented to the user, not to purposely scare them based on their fears and trepidations, but to help the user get through these situations if ever faced with them, and to expose them to the situation in a safe, controlled environment.

For example, the scenarios may include: a scenario of a home invasion, and how a person may work through that situation while protecting themselves and their family; the scenario of being in a school with an active shooter, and how a person may work through that situation in the safest possible manner; or the scenario of a burning building, and how a person may get themselves to safety without injury or death. The scenarios may further include being on a top floor of a building that is on fire, being inside a school where there is an active shooter, waking up to find somebody has broken into the user's home and is still there, a phobia of spiders, a phobia of heights, being lost in a forest, simulating drowning, being in a natural disaster (e.g., an earthquake, a tornado, a hurricane, and/or a tsunami), and/or being a passenger on a plane.

The situations may further include new situations that allow the user to overcome more "commonplace" fears including, but not limited to: phobias dealing with the fear of a variety of animals; phobias pertaining to fear of heights, flying, and other motion-related activity; or phobias dealing with clowns, ghosts, and other "people-related" fears.

For example, the method may be used by therapists with their patients to overcome the phobias mentioned above, as well as many others. In accordance with the present disclosure, patients can be exposed to and treated for these fears in a safe and controlled environment. For example, the method may be used by school districts to use as a prevention tool for students, where they can learn how to deal with a school shooting scenario and safely follow procedures if they are unfortunate enough to be presented with that situation.

The disclosed technology has the benefit of having users experience a simulated stressful situation, without the inherent danger of an actual stressful situation.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in various embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

Any of the herein described methods, programs, algorithms, or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages that are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood the foregoing description is only illustrative of the present disclosure. Various alternatives and modifications can be devised by those skilled in the art without departing from the disclosure. Accordingly, the present disclosure is intended to embrace all such alternatives, modifications, and variances. The embodiments described with reference to the attached drawing figures are presented only to demonstrate certain examples of the disclosure. Other elements, steps, methods, and techniques that are insubstantially different from those described above are also intended to be within the scope of the disclosure.

What is claimed is:

1. A system for display for an augmented/virtual reality-based decision-making simulation comprising:
a controller configured to receive input from a user;
at least one of an augmented reality or a virtual reality device configured to display a simulated environment;
a processor; and
a memory coupled to the processor and storing one or more computer-readable instructions, wherein the computer-readable instructions cause, when executed by the processor, the system to:
receive at least one of a user preference, user task, historical data, or past weather from a web interface of the system;
receive user input from the controller indicating a selected scenario, wherein the selected scenario includes at least one of: being in a building that is on fire, waking up to find somebody has broken into a home of the user and is still there, being lost in a forest, simulating drowning, or being in a natural disaster;
display the selected scenario on the at least one of the augmented reality or the virtual reality device;
receive input from the controller indicating user interaction with the selected scenario;
monitor one or more parameters associated with the execution of tasks in the selected scenario using the controller; and evaluate the user based on the monitored one or more parameters and the at least one of the user preference, user task, historical data, or past weather;

display, on at least one of the augmented reality or the virtual reality display, a layout of decisions that were made by the user during the selected scenario, the layout of decisions including a percentage-based score indicating a chance of survival based on the layout of decisions, wherein the layout of decisions masks feedback on individual decisions.

2. The system of claim 1, wherein the evaluation is performed using machine learning.

3. The system of claim 1, wherein the instructions, when executed by the processor, further cause the system to:
display, on at least one of the augmented reality or the virtual reality display, a walk-through of the layout.

4. The system of claim 1, wherein the instructions, when executed by the processor, further cause the system to:
display, on at least one of the augmented reality or the virtual reality display, an indication of how one or more major decisions impacted an outcome of the selected scenario.

5. The system of claim 1, further comprising a heart rate monitor configured to generate a signal indicative of a heart rate of the user.

6. The system of claim 5, wherein the instructions, when executed by the processor, further cause the system to:
receive the signal from the heart rate monitor; and
modify the simulated environment based on the signal, wherein modifying the simulated environment includes modifying a difficulty level of the selected scenario.

7. The system of claim 5, wherein the instructions, when executed by the processor, further cause the system to:
display on the at least one of the augmented reality or the virtual reality device an indication of the input chosen by the user.

8. The system of claim 1, wherein the at least one of the augmented reality or the virtual reality device further includes a sensor configured to sense head movement and communicate to the processor a signal indicative of a head movement of the user, and
wherein the instructions, when executed by the processor, further cause the system to:
receive further input from the at least one of the augmented reality or the virtual reality device based on the user's head movements; and
move the user in the simulated environment based on the further input.

9. The system of claim 1, wherein the instructions, when executed by the processor, further cause the system to:
receive input from the controller indicating a selection of an alternative decision for the selected scenario, wherein the alternative decision is different than a corresponding decision in the layout of decisions.

10. The system of claim 1, wherein the instructions, when executed by the processor, further cause the system to:
display, on at least one of an augmented reality or a virtual reality display, a fluctuation of the percentage-based score based on each decision within the layout of decisions.

11. A computer-implemented method for an augmented/virtual reality-based decision-making simulated environment, the method comprising:
receiving at least one of a user preference, user task, historical data, or past weather from a web interface;
receiving, from a controller configured to receive input from a user, user input indicating a selected scenario, wherein the selected scenario includes at least one of: in a building that is on fire, waking up to find somebody has broken into a home of the user and is still there, being lost in a forest, simulating drowning, or being in a natural disaster;
displaying, on at least one of an augmented reality or a virtual reality device, the selected scenario;
receiving input from the controller indicating user interaction with the selected scenario;
monitoring one or more parameters associated with the execution of tasks in the selected scenario using the controller; and
evaluating the user based on the monitored one or more parameters and the at least one of the user preference, user task, historical data, or past weather; and
displaying, on at least one of the augmented reality or the virtual reality display, a layout of decisions that were made by the user during the selected scenario, the layout of decisions including a percentage-based score indicating a chance of survival based on the layout of decisions, wherein the layout of decisions masks feedback on individual decisions.

12. The computer-implemented method of claim 11, wherein the evaluation is performed using machine learning.

13. The computer-implemented method of claim 11, further comprising:
displaying, on at least one of the augmented reality or the virtual reality display a walk-through of the layout.

14. The computer-implemented method of claim 11, further comprising:
displaying, on at least one of the augmented reality or the virtual reality display an indication of how one or more major decisions impacted an outcome of the selected scenario.

15. The computer-implemented method of claim 11, further comprising:
receiving a signal from a heart rate monitor configured to generate a signal indicative of a heart rate of the user; and
modifying the simulated environment based on the signal, wherein modifying the simulated environment includes modifying a difficulty level of the selected scenario.

16. The computer-implemented method of claim 11, wherein the at least one of the augmented reality or the virtual reality device further includes a sensor configured to sense head movement, and
wherein the computer-implemented method further comprises:
receiving further input from the at least one of the augmented reality or the virtual reality device based on the user's head movements; and
moving the user in the simulated environment based on the further input.

17. The computer-implemented method of claim 11, further comprising:
displaying on the at least one of the augmented reality or the virtual reality device an indication of the input chosen by the user.

18. A non-transitory computer-readable storage medium in which is stored instructions for causing a processor to execute a computer-implemented method for an augmented/virtual reality-based decision-making simulated environment, the method comprising:
receiving at least one of a user preference, user task, historical data, or past weather from a web interface;
receiving, from a controller configured to receive input from a user, user input indicating a selected scenario, wherein the selected scenario includes at least one of: being in a building that is on fire, waking up to find somebody has broken into a home of the user and is still there, being lost in a forest, simulating drowning, or being in a natural disaster;

displaying, on at least one of an augmented reality or a virtual reality display, the selected scenario;

receiving input from the controller indicating user interaction with the selected scenario;

monitoring one or more parameters associated with the execution of tasks in the selected scenario using the controller; and evaluating the user based on the monitored one or more parameters and the at least one of the user preference, user task, historical data, or past weather; and displaying, on at least one of the augmented reality or the virtual reality display, a layout of decisions that were made by the user during the selected scenario, the layout of decisions including a percentage-based score indicating a chance of survival based on the layout of decisions, wherein the layout of decisions masks feedback on individual decisions.

\* \* \* \* \*